(12) United States Patent
Crawford

(10) Patent No.: US 11,759,535 B2
(45) Date of Patent: Sep. 19, 2023

(54) WEARABLE DECONTAMINATION SYSTEM

(71) Applicant: Mark Crawford, Paducah, KY (US)

(72) Inventor: Mark Crawford, Paducah, KY (US)

(*) Notice: Subject to any disclaimer, the term of this patent is extended or adjusted under 35 U.S.C. 154(b) by 330 days.

(21) Appl. No.: 17/246,526

(22) Filed: Apr. 30, 2021

(65) Prior Publication Data
US 2021/0353788 A1 Nov. 18, 2021

Related U.S. Application Data

(60) Provisional application No. 63/025,012, filed on May 14, 2020.

(51) Int. Cl.
*A61L 2/00* (2006.01)
*A61L 2/26* (2006.01)

(52) U.S. Cl.
CPC ............... *A61L 2/0088* (2013.01); *A61L 2/26* (2013.01); *A61L 2202/15* (2013.01); *A61L 2202/16* (2013.01)

(58) Field of Classification Search
CPC ...... A61L 2/0088; A61L 2/26; A61L 2202/15; A61L 2202/16; A47K 5/1201; A61M 35/003; B05B 11/0008; B05B 11/0056; B05B 11/0038; B05B 11/0062; B05B 11/026; B05B 11/1032
See application file for complete search history.

(56) References Cited

U.S. PATENT DOCUMENTS

| | | | | |
|---|---|---|---|---|
| 4,629,098 A * | 12/1986 | Eger | ........................ | A45F 5/00 222/530 |
| 5,484,085 A * | 1/1996 | Bennett | .................... | F41H 9/10 222/530 |
| 5,503,304 A * | 4/1996 | Keller | ...................... | F41H 9/10 222/630 |
| 5,538,164 A * | 7/1996 | Rivas | ....................... | F41H 9/10 222/153.04 |
| 5,607,090 A * | 3/1997 | Brown | ..................... | A45C 1/04 224/217 |
| 5,678,730 A * | 10/1997 | Fabek | .................... | B65D 83/75 222/402.15 |
| 6,123,228 A * | 9/2000 | Hippensteel | .............. | F41H 9/10 222/402.11 |
| 6,814,260 B2 * | 11/2004 | Caffrey | ................. | B05B 9/0811 446/475 |
| 9,888,816 B1 * | 2/2018 | Shaukat | ............... | A47K 5/1204 |
| 2015/0216367 A1 * | 8/2015 | Barbier | ................ | A47K 5/1201 222/1 |

* cited by examiner

*Primary Examiner* — Vishal Pancholi
(74) *Attorney, Agent, or Firm* — Chris Tanner; TannerPatent.com

(57) ABSTRACT

A same-hand, finger-mounted, and finger-operated hand sanitizer dispensing system with finger-mounted or with remote-mounted fluid reservoir, is disclosed herein. The system is operable without risk of cross-contamination, and is operable by the contaminated hand for self-decontamination. A dispensing pump is mounted on one finger and operated by another finger on the same hand. The dispensing pump draws sanitizer from a reservoir by way of a supply tubing. The reservoir can be mounted on the same finger as the pump or on another finger of the same hand.

19 Claims, 12 Drawing Sheets

WEARABLE DECONTAMINATION SYSTEM

BACKGROUND

The embodiments herein relate generally to hand sanitizer liquid dispensing devices and, more particularly, to a wearable hand sanitizer dispenser and a procedure and method for using that apparatus to dispense a quantity of hand sanitizer directly into the hand of the wearer.

Communicable diseases are commonly transferred person-to-person by airborne spread or by contact spread of the infecting bacteria or virus. Airborne spread occurs when an infected individual coughs or sneezes, expelling infectious droplets or aerosols which are then inhaled by another person. Contact spread occurs when an infected individual contaminates with infectious material a surface on another person or object by cough or sneeze or touch. A second person then touches that contaminated surface, usually with his fingers, and then transfers that infectious material to his eyes, nose, or mouth, whereby that infectious material enters the body thus infecting that second person.

Infectious material can also be transferred from a contaminated surface to an uncontaminated surface by a person touching the contaminated surface and then touching an uncontaminated surface. The second surface is now also contaminated with the infectious agent. This process is known as cross-contamination. Any person who happens to touch that second cross-contaminated surface is then at risk of contracting the disease and of further cross-contaminating other surfaces and further spreading the disease.

The prevention of contact spread is a major objective in arresting the spread of communicable, pandemic diseases and employs several methods. A first method is regular disinfection of potentially contaminated surfaces with chemical disinfectants or with ultraviolet light. A disadvantage of this method is that a surface can be quickly re-contaminated and then transfer the disease before that surface is again disinfected. It is also logistically difficult to regularly disinfect all potentially contaminated surfaces in the human environment.

A second method of preventing contact spread is wearing gloves. Gloves have several disadvantages. Gloves may be free of infectious material when first worn but, like bare hands, become contaminated as soon as they come into contact with a contaminated surface. In order to prevent cross-contamination, gloves must be discarded or, as with bare hands, chemically sanitized. Gloves therefore offer limited advantage over bare hands in the prevention of disease contact spread. Frequent glove changes can become expensive. In a pandemic, glove supplies can become quickly exhausted. Gloves impair hand dexterity, are hot, and cause hands to sweat, all of which discourage their wear by the general public.

A third method is hand-washing with soap and water, which is cheap and effective. The major disadvantage to this method is lack of readily available facilities for hand-washing with soap and water.

A fourth method of preventing contact spread is decontaminating the hands with a hand sanitizer chemical. In order to be most effective a hand sanitizer dispenser, must be immediately available, must be operable without cross-contamination, and must be capable of a contaminated hand independently decontaminating itself without assistance from the other hand. Immediate availability enables a hand to be decontaminated immediately following contamination. The longer the delay in hand decontamination, the greater the likelihood of unintended face-touching or surface cross-contamination. Dispensing without cross-contamination requires that a single hand or both hands be decontaminated without those hands contaminating the person's clothing, other objects such a purse, or the dispenser itself in the course of dispenser retrieval and actuation. Independent hand decontamination enables a contaminated hand to sanitize itself Commonly only a single hand touches a surface and is contaminated, while the opposite uncontaminated hand is often performing other tasks such as carrying an object or a child or even holding a child's hand. In order for this opposite hand to participate in sanitizing the contaminated hand, it must discontinue its current task. The object or child must be placed somewhere else, or the child's hand released, all of which entail further decisions and hazards. Hand sanitizer use at such a time is thus discouraged.

In the effort to reduce hospital-acquired infections, hospitals have long recognized the critical importance of hand sanitizer being immediately available, dispensed without cross-contamination, and operated by each hand independently. Hospitals try to achieve immediate availability by placing wall-mounted sanitizer dispensers in multiple locations throughout the hospital, particularly including inside and outside every patient room. They try to achieve dispensing without cross-contamination and independent hand operation by using wall-mounted dispensers that are motion-activated.

A motion-activated sanitizer dispenser for portable, personal use would also have several disadvantages. It would require batteries, which add weight and bulk and which eventually become drained, rendering the dispenser inoperable. Motion-activated devices also suffer the common disadvantage of unintended activation by extraneous movement. This problem would be exacerbated in a body-worn device.

Individuals commonly improve on sanitizer availability by carrying a capped, squeeze, or pump dispenser on their person or in a purse. Retrieving the container typically requires moving clothing about and reaching into a pocket or purse. The time and effort required in this retrieval process can thus discourage and delay sanitizer use. Therefore such personally-carried dispensers do not achieve the desired immediate availability.

As just described, in many cases where one hand is contaminated, a personally-carried dispenser is stowed in a pocket or purse not readily accessible by the uncontaminated hand. In many other instances, both hands are required to retrieve the container, or both hands may already be contaminated. All of these instances can result in cross-contamination of clothing, personal items, the opposite hand, and the sanitizer dispenser itself. Therefore such personally-carried dispensers do not achieve the desired operation without risk of cross-contamination.

Most, if not all, personally-carried sanitizer dispensers require the use of both hands. One hand holds the bottle while the other opens it up. The contaminated hand is held under the dispensing nozzle while the opposite hand inverts and squeezes the bottle or operates the pump. The use of the opposite hand necessarily stops any task performance by that hand. Therefore such personally-carried dispensers do not accomplish the goal of self-sanitizing the contaminated hand.

A hand sanitizer dispenser can attempt to overcome these limitations by being worn on clothing or on the body itself. The utility of garment-mounted dispensers can be diminished by overcoats, raincoats, and jackets which might be taken off and on throughout a day. The dispenser may be removed with the garment, limiting immediate availability.

A contaminated hand must be brought in close proximity to any garment-mounted dispenser in order to receive the sanitizer or to operate the dispenser, thus risking cross-contamination of clothing and dispenser.

A dispenser worn or mounted on an exposed body area might possibly allow dispenser access without garment cross-contamination. Body areas that are most commonly exposed are the face, neck, and hands. The face and neck are the last places one would want to mount a hand sanitizer dispenser since a main objective of hand sanitation is to keep contaminated hands away from the face. A wrist-mounted dispenser might be considered, but wrist exposure varies with the season and long-sleeve wear. Long-sleeved garments may require pushing up the sleeve to access a wrist-mounted dispenser, making that dispenser not immediately available. Having to push up a sleeve also risks garment cross-contamination. A wrist-mounted dispenser must be operated by the opposite hand, as the fingers of a hand cannot reach its wrist. A wrist-mounted dispenser is thus not capable of one-handed independent operation. Task performance of the opposite hand is thus impaired. And when both hands are contaminated, the difficulty in avoiding cross-contamination is doubled.

Consequently, a need exists for a portable, personally-carried hand sanitizer dispenser that (1) is immediately and quickly available to a person in almost any situation or person, (2) is operable without risk of cross-contamination of garments, uncontaminated body parts, or other objects, and (3) allows one hand to decontaminate itself, leaving the other hand free to perform other tasks.

DETAILED DESCRIPTION OF THE PREFERRED EMBODIMENTS

Figure 1:
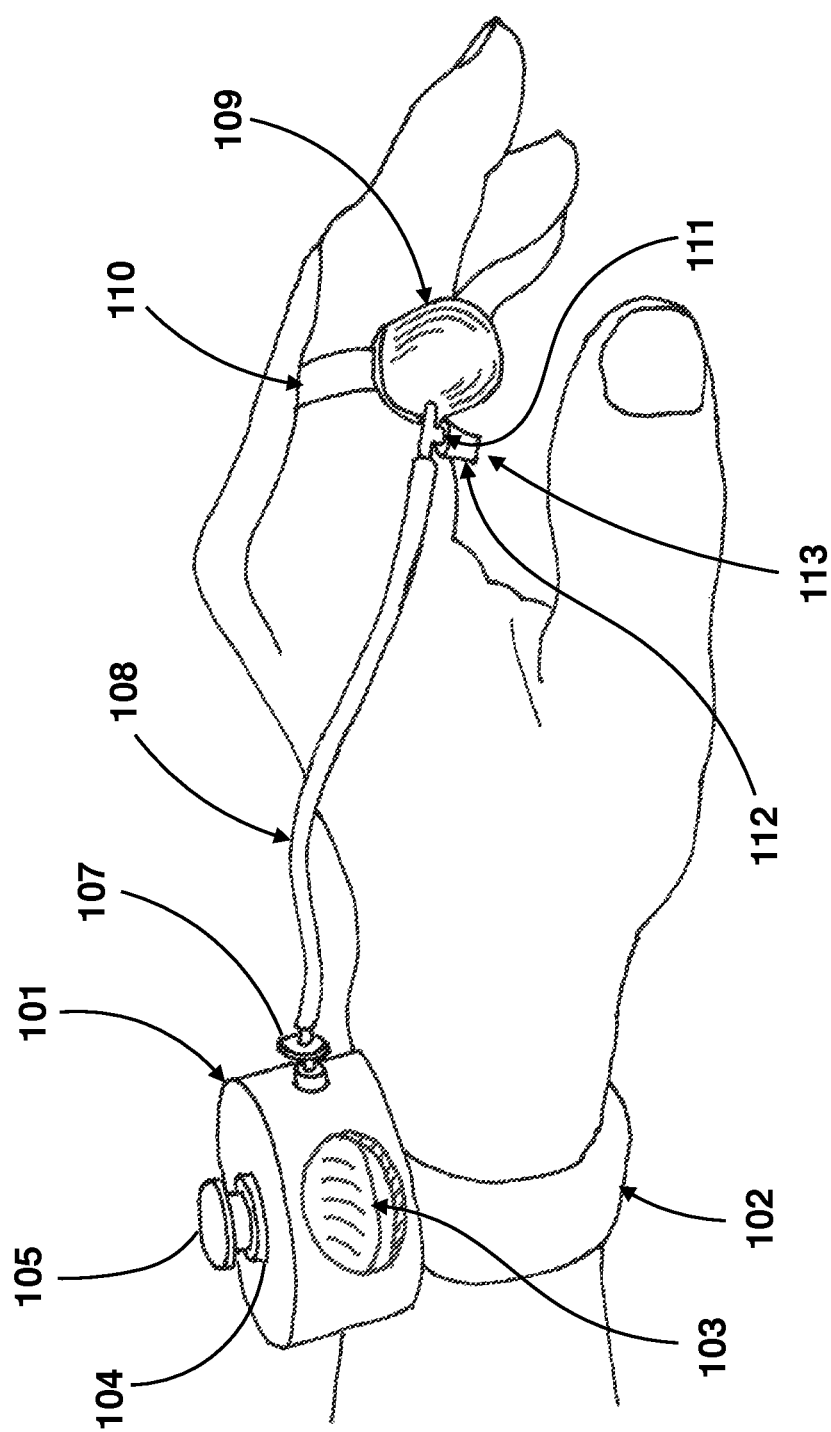
FIG. 1 is a perspective view of a hand decontamination system according to a preferred embodiment.

Before explaining the disclosed embodiment of the present embodiments herein in detail, it is to be understood that the embodiments herein is not limited in its application to the details of the particular arrangement shown, since the embodiments herein is capable of other embodiments. Also, the terminology used herein is for the purpose of description and not of limitation.

Foundation and Context

A same-hand, finger-mounted, and finger-operated hand sanitizer dispensing pump with finger-mounted or with remote-mounted fluid reservoir, such as within the embodiments disclosed herein, is immediately available to a person, is operable without risk of cross-contamination, and is operable by the contaminated hand for self-decontamination. A dispensing pump is mounted on one finger and operated by another finger on the same hand. The pump draws sanitizer from a reservoir by way of a supply tubing. The reservoir can be mounted on the same finger as the pump or on another finger of the same hand. If a reservoir of capacity too large for a finger is desired, then the reservoir can be remotely-mounted such as on the wrist or forearm or however far one wishes to run the supply tubing.

The principles of finger-mounting described herein require only the press of a finger of the contaminated hand to dispense sanitizer into the palm of that hand. No retrieving from pockets or purses is required. No touching a garment or other body areas is required. Opening a container is not required. Requiring only the press of a finger, a same-hand finger-mounted, finger-operated hand sanitizer dispenser is thus immediately available.

The hand being an exposed body area, hand-mounting a sanitizer dispensing pump avoids the cross-contamination risks of garment-mounting. Hand-mounting also avoids the cross-contamination risks of mounting on other exposed body areas including wrists, face, and neck. As the fingers on the contaminated hand rub and disperse the sanitizer over that hand, those fingers can at the same time rub sanitizer over the pump itself. Dispenser cross-contamination is thus mitigated. A same-hand, finger-mounted, finger-operated hand sanitizer dispenser is thus operable without cross-contamination.

Using the embodiments herein, when a single hand is contaminated, the finger-mounted dispensing pump on that hand can be actuated by another finger on that contaminated hand. Sanitizer is dispensed into the palm of the contaminated hand. The fingers of that hand can then rub and distribute the sanitizer over those areas of the fingers and hands that are commonly contaminated after touching a contaminated surface, as well as over the pump itself. The opposite hand is neither required to operate the pump nor to rub and distribute the sanitizer and remains free to continue with other tasks. A same-hand, finger-mounted, finger-operated hand sanitizer dispenser is thus one-hand independently operable.

This finger-mounted pump can also be worn over gloves, thereby offering the same advantages of immediate availability, operation without cross-contamination, and hand self-decontamination. In addition to these advantages, the frequency of glove changes can be reduced, which in turn reduces glove expense and depletion of glove supply.

A typical personally-carried hand sanitizer dispenser must be inverted and squeezed or held upright and pumped in order to dispense sanitizer. Air is then drawn into the container to replace the volume of sanitizer dispensed. Failure to admit air creates a vacuum, which can collapse the container and impair further dispensing. A wearable dispenser should be operable in any position; otherwise immediate availability and ease of use is impaired. The embodiments herein therefore use a fluid reservoir that is constructed of flexible material, such as a plastic intravenous fluid bag, that allows the reservoir to collapse rather than to admit air as sanitizer is used.

Within the embodiments herein, the sanitizing fluid can be made to flow from a reservoir by gravity or by pump. Gravity flow requires the reservoir to be elevated higher than the palm when the sanitizer is being dispensed. This undesirable limitation is overcome by using a pump that can generate sufficient pressure to deliver sanitizer from a reservoir at any elevation in relation to the palm. Therefore the embodiments herein utilize a pump.

A finger-mounted pump can be electrically or manually operated. Electrical operation is undesirable because batteries add weight and bulk and can run down. Manual pumps can be piston or bulb pumps. Piston pumps require several parts, including cylinder, piston, seals, and plunger. Bulb pumps are a single part. For a given quantity of fluid constrained within a given geometric shape such as a cylinder, a piston pump will have greater bulk than a bulb pump. This greater bulk is because the piston pump has the added height of the piston and plunger which the bulb pump does not. In the bulb pump, the bulb wall acts as the de-factor "piston" and the operating finger acts as the de-facto "plunger". The embodiments herein therefore utilize a bulb pump.

A bulb pump requires check valves to control the direction of fluid flow, in this instance from reservoir to pump to a discharge orifice where a stream of sanitizer is sprayed into the palm. A first discharge check valve allows fluid flow from pump to discharge orifice when the pump is depressed. A second intake check valve allows fluid flow from reservoir to pump when the pump is released. Check valves come in several designs, including ball, diaphragm, swing, lift, and duckbill, with choice dictated by size, flow, and pressure limits. Check valves have a minimum opening pressure or cracking pressure. Within the embodiments herein, the fluid reservoir will at times be at a higher elevation than the discharge orifice. Gravity pressure could then generate sufficient pressure to crack open the check valves, causing unwanted fluid flow. The embodiments herein thus require a discharge check valve of sufficiently high cracking pressure to prevent a gravity-induced, undesirable fluid flow. The embodiments herein therefore utilize suitable intake and discharge check valves.

A flexible, collapsible fluid reservoir bag, as in the present embodiments herein, can be inadvertently squeezed or leaned on, thus generating sufficient pressure to open both check valves and resulting in undesirable fluid flow. This problem can be overcome by placing the reservoir bag in a rigid housing. The embodiments herein therefore utilize a rigid reservoir housing.

FIG. 1 shows a rigid reservoir housing 101 attached to a wrist by mounting strap 102 and containing a flexible, collapsible fluid reservoir bag 103 having a filler bag port 104 sealed by a filler port plug 105 and a supply bag port 106 filled by a pump intake check valve 107. A pump supply tube 108 connects fluid reservoir bag 103 and intake check valve 107 to a finger-mounted bulb pump 109 attached to an index finger by an adjustable-ring pump mount 110. A pump discharge tube 111 connects bulb pump 109 to discharge check valve 112 and discharge orifice 113.

In order for a hand-mounted pump to be operated by a movement of that same hand, it must be operated by a movement of a finger on that hand, as no other suitable movement sources are available on the hand. The pump must therefore be located where it is anatomically accessible by a finger on that hand. It is further advantageous that the pump be located on the hand where it does not interfere or impede normal hand functions. Pump location determines pump design. Accordingly, the pump, tubing, check valves, and discharge fittings disclosed herein are customized to fit the anatomy of that particular location while avoiding impairing hand functions.

Determining a suitable pump location therefore requires an understanding and explanation of basic hand anatomy and function. The hand has five digits or fingers including thumb, index, long, ring, and small. The hand and fingers each have a front side or palmar surface, and a back side or dorsal surface. The hand and fingers each have a side toward the thumb or radial side, and a side toward the small finger or ulnar side. The surfaces of each finger can be divided along the length of the finger by reference to the particular finger bone underlying that segment of the finger. The thumb has two bones or phalanges, the proximal phalanx closer to the base of the thumb and a distal phalanx closer to the tip of the thumb. The remaining four fingers each have three bones: the proximal phalanx nearest the base, the distal phalanx nearest the tip, and the middle phalanx in between these two.

The hand has three major functions, namely touching, gripping, and pinching. Touching is usually performed with the touch surfaces of the hand which are primarily the palmar surfaces of the hand and fingers. Gripping is the holding or grasping of an object, such as a broom handle, by curling the thumb around the object from one direction and curling the remaining fingers around the object from the opposite direction. The hand and finger surfaces that are in contact with the object are the gripping surfaces.

Pinching has two main forms: two-point pinch and key pinch. Two-point pinch is the grasping of an object, such as a coin, between the palmar surfaces of the tips of the thumb and of the index fingers. Key pinch is the grasping of an object, such as a key, between the palmar surface of the thumb overlying its distal phalanx and the radial surface of the adjacent index finger overlying the distal and middle phalanges. These finger surfaces that are in contact with a pinched object are the pinching surfaces.

In order to avoid impairing hand functions, a hand sanitizer dispensing pump cannot be located on the touch, grip, or pinch surfaces of the hand or fingers. Thus the palmar surfaces of the hand and of all fingers and the radial surface of the index finger at middle and distal phalanx levels are not suitable pump locations. In gripping, the spaces between the index, long, ring, and small fingers narrow until the fingers are touching as they curl around the gripped object. No room is left between these fingers to accommodate a pump during gripping. The surfaces between these four fingers are therefore not suitable pump locations.

Within the embodiments herein, the anatomical determinate of effective location of the pump location is finger reach. The dorsal surfaces at the distal phalanx level of all five fingers are unsuitable, as any mounted pump could too easily slip off the tapered fingertips. The thumb can reach the dorsal surfaces at the middle phalanx level of the four other fingers, but doing so requires those fingers to be curled down tightly into the palm. Insufficient room is left in the palm to receive dispensed hand sanitizer, making these surfaces not suitable pump locations. The dorsal surface of the thumb at the proximal phalanx level is accessible to the index finger; however it requires the thumb to be flexed in an awkward position. Additionally, the index finger cannot pinch down squarely on this surface, which is required for compressing a piston or bulb pump. The index finger can only obliquely graze this surface. This dorsal thumb location is therefore not a suitable pump location.

The functional limitations of touch, grip, and pinch and the anatomical limitations of finger reach thus leave only one suitable location for the hand-mounted sanitizer dispensing pump described herein, namely the radial surface of the index finger at the proximal phalanx level. This location is not a "touch surface" so a pump located on this surface will not impair touch.

Figure 2A:
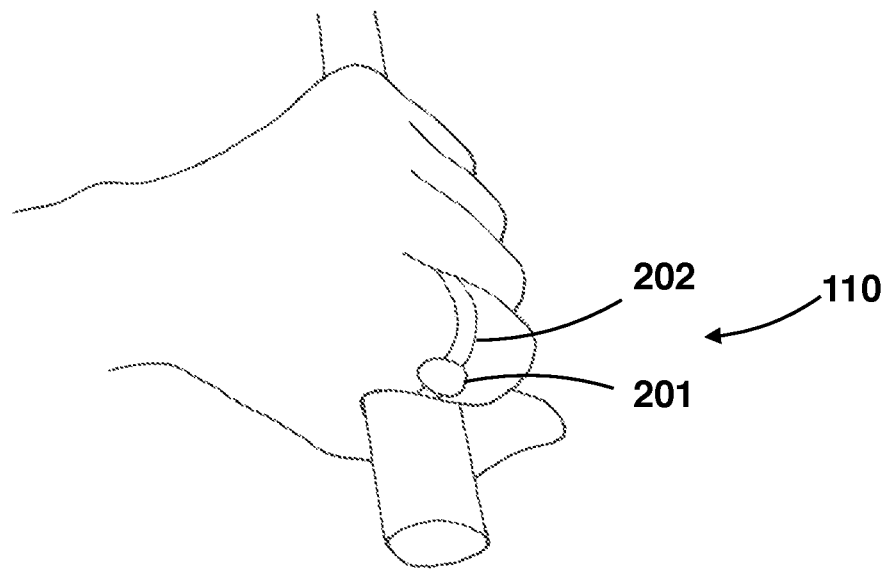
FIG. 2A is a perspective view of a hand in a gripping position along with an index finger pump mount.

FIG. 2A shows adjustable-ring pump mount 110 located on an index finger at the proximal phalanx level. Accordingly, the pump mount 110 includes an adjustable ring 201 around the finger and a mounting surface 202 where a pump can be located. The mounting surface 202 is located at the suitable pump location on the radial surface. As FIG. 2A shows, this mounting surface 202, and in turn any pump mounted on it, does not encroach on a gripping surface. Unlike the spaces between the remaining fingers, the space between thumb and index fingers remains wide during gripping, leaving sufficient space for a pump. A pump located on this surface will not impair grip.

Figure 2B:
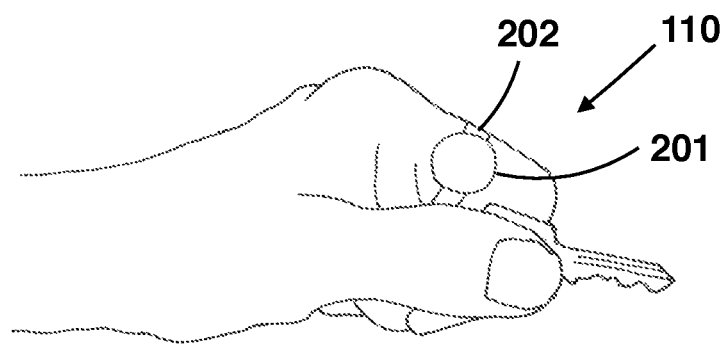
FIG. 2B is a perspective view of a hand in a key pinch position along with an index finger pump mount.
Figure 2C:
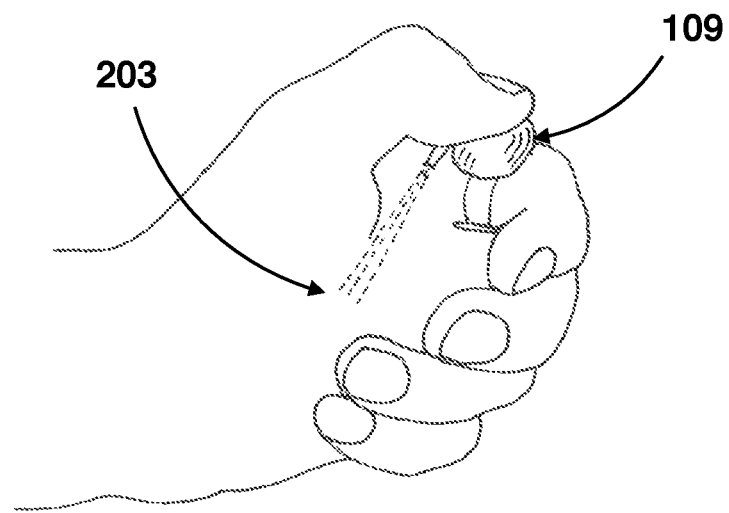
FIG. 2C is a perspective view of a hand in a closed palm position along with an index finger-mounted dispensing bulb pump being operated by the thumb.
Figure 2D:
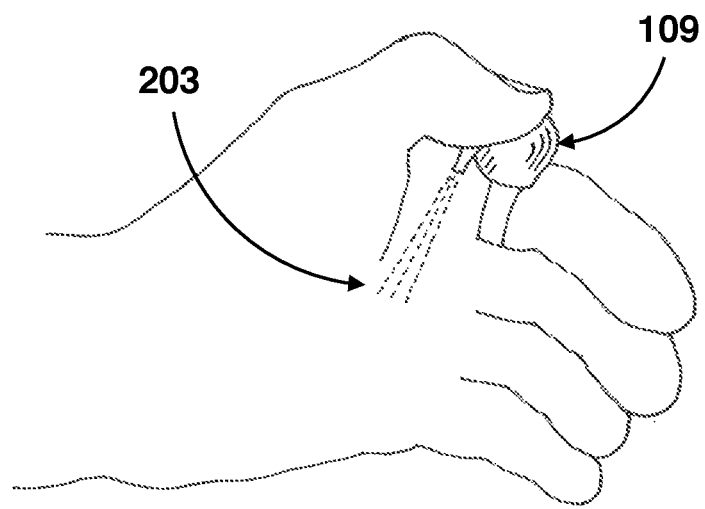
FIG. 2D is a perspective view of a hand in an open palm position along with an index finger-mounted dispensing bulb pump being operated by the thumb.

As shown in FIG. 2B, the mounting surface 202, and any pump located on it, does not encroach on a pinch surface and does not contact the thumb in key pinch. A pump located on this finger surface will not impair pinch. As shown in FIG. 2C, the thumb can squarely compress a bulb pump 109 located on this surface with the remaining fingers flexed to sufficiently close the palm to catch a sanitizer spray stream 203. As shown in FIG. 2D, the thumb can squarely compress a bulb pump 109 located on this surface with the remaining fingers extended to sufficiently open the palm, allowing sanitizer spray stream 203 to be directed to the opposite hand or to the hand of another individual.

An additional issue regarding the pump location described above requires a width of a pump be no wider than the width of an index finger at the proximal phalanx level in order to avoid hanging down toward the palmar surface and encroaching on touch and grip surfaces. Pump height should be short enough to avoid impinging on the adjacent thumb. Since the pump should be as compact as possible, a bulb pump is preferred over a piston pump, as previously stated.

Figure 3A:
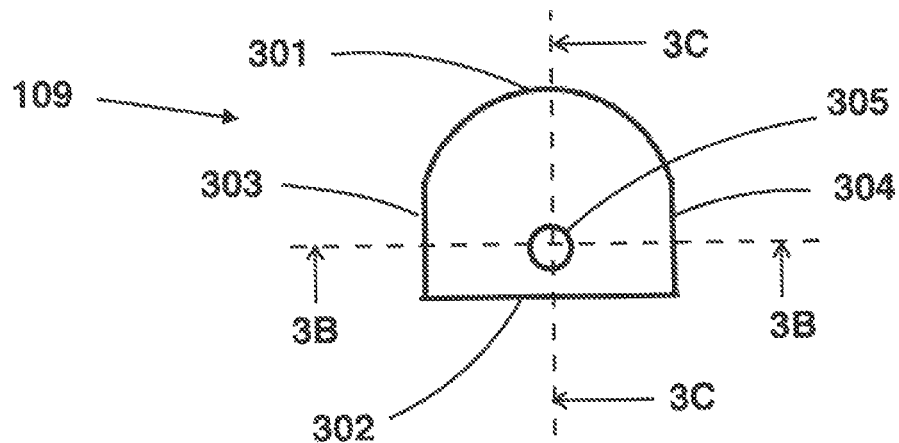
FIG. 3A is a frontal view of a dispensing bulb pump.
Figure 3B:
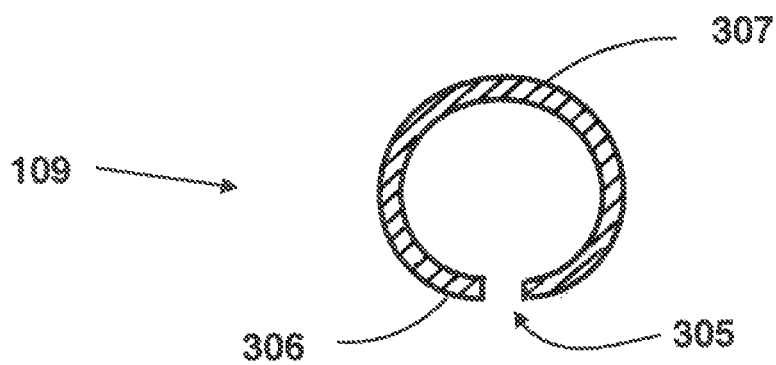
FIG. 3B is a sectional view of a dispensing bulb pump taken along line 3B-3B of FIG. 3A.
Figure 3C:
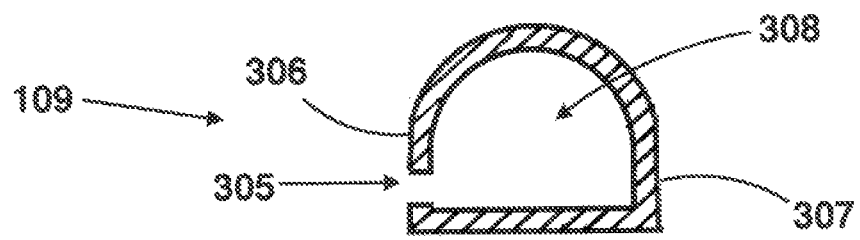
FIG. 3C is a sectional view of a dispensing bulb pump taken along line 3C-3C of FIG. 3A.

Bulb pumps commonly have a supply tube on one side and a discharge tube on the opposite side of the pump. This configuration takes up more length than a bulb pump with a tube on one side only. Such a tubing arrangement at the index finger, radial-side, proximal phalanx location could result in tubing encroaching on the adjacent key pinch surface. Therefore, as shown by bulb pump 109 in FIG. 1, the embodiments herein utilize a bulb pump with tubing entering a single side only. FIG. 3A shows bulb pump 109 having a top side or dome 301, a bottom side or base 302, a left side 303, a right side 304, and a tube port 305. FIG. 3B shows bulb pump 109 having a front side 306 and a back side 307. FIG. 3C is a sectional view of a dispensing bulb pump taken along line 3C-3C of FIG. 3A, showing the bulb pump 109 having an interior cavity 308.

Designing a hand decontamination system around a dispensing pump mounted at this one suitable hand location requires understanding the system components and their functions. As shown in FIG. 1, when the bulb pump 109 is depressed, fluid is forced out of the pump. Retrograde fluid flow through supply tube 108 then pushes the check valve 107 closed, thereby preventing flow into fluid reservoir bag 103. Ante-grade fluid flow through discharge tube 111 which pushes the discharge check valve 112 open, allowing fluid to be dispensed out of discharge orifice 113. When bulb pump 109 is released, fluid is drawn into the re-expanding bulb pump 109. Retrograde fluid flow through discharge tube 111 draws discharge check valve 112 closed. Ante-grade fluid flow through the supply tube 108 draws the intake check valve 107 open, allowing fluid to flow out of the reservoir bag and into the pump.

It will be no surprise to the reader that space for check valves at the index finger location is limited. Accordingly, the intake check valve 107, with tubing arranged as shown in FIG. 1, can be located anywhere between fluid reservoir bag 103 and the branching off of discharge tube 111.

It is a feature of the embodiments herein that the fluid reservoir bag 103 is not located at the pump location. Instead, the reservoir bag 103 can be located at multiple sites including the dorsal surface of the index finger, the wrist, or the forearm. All of these reservoir bag locations have much more room to accommodate system components than at the bulb pump location. Accordingly, as depicted in FIG. 1, the intake check valve in this system is located at the fluid reservoir bag 103.

As shown in FIG. 1, discharge check valve 112 can be located anywhere between the branching off of discharge tube 111 and discharge orifice 113. It is desirable for sanitizer to be dispensed into the palm of the hand where all fingers can access the dispensed pool of sanitizer and (through movement of all fingers) distribute the sanitizer over the contaminated touch surfaces of that hand. A pump mounted on this index finger, radial-side, proximal phalanx surface is immediately adjacent to the palm as shown in FIGS. 2C and 2D. This pump mounting location therefore dictates that the connection between bulb pump 109 and discharge orifice 113 be as short in length as possible. The greater the length of the components required for making this connection, the greater the risk of impinging on the palm and thus impairing gripping.

Figure 4:
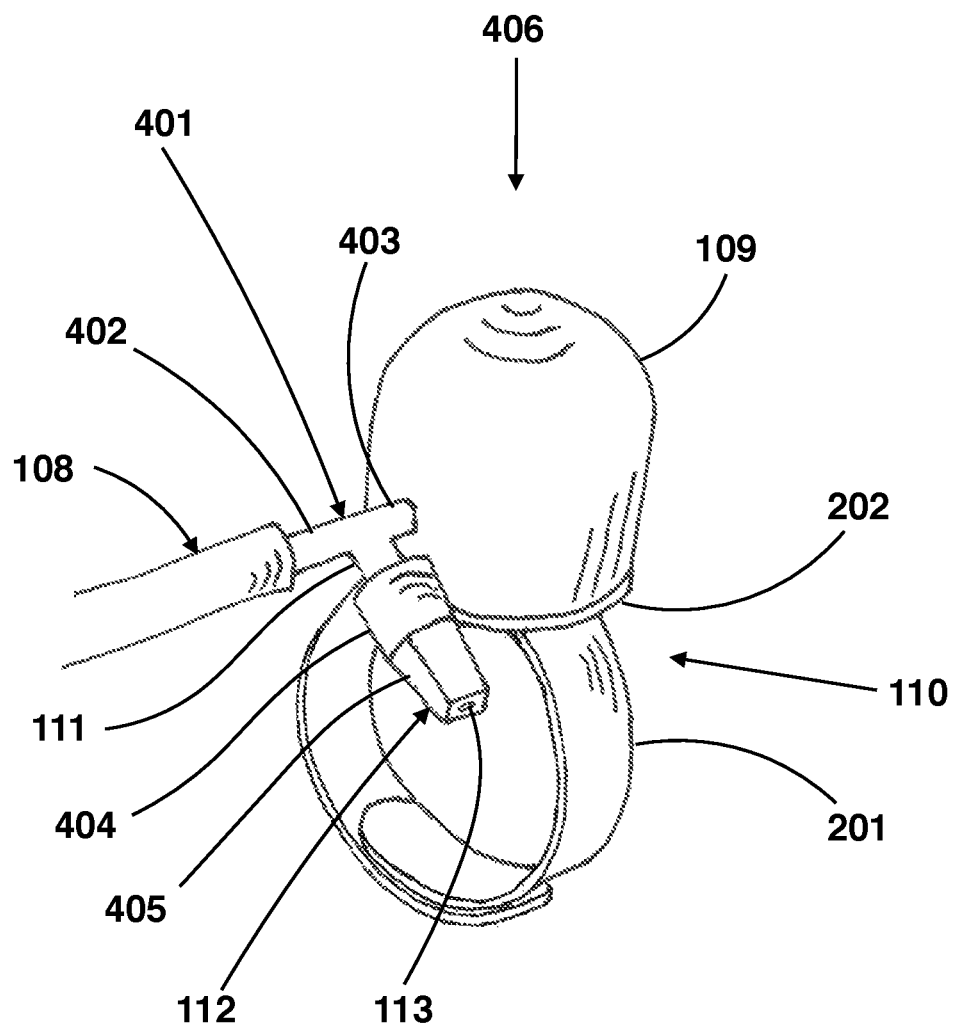
FIG. 4 is a perspective view of a pump assembly including a dispensing bulb pump, tubing connector, discharge check valve, and adjustable-ring pump mount.

FIG. 4 shows one potential embodiment for incorporating these desirable dispensing pump features in a hand decontamination system. A pump assembly 406 includes a bulb pump 109, a pump mount 110 having an adjustable ring 201 and a mount surface 202, a barbed T-fitting 401 having a supply branch 402, a pump branch 403, and a discharge tube 111, and a discharge check valve 112. The supply branch 402 and the pump branch 403 of the T-fitting 401 connect supply tube 108 to bulb pump 109 by way of tube port 305. The discharge tube 111, the remaining branch of T-fitting 401, connects pump 109 to discharge orifice 113. The discharge check valve 112 mounts directly onto discharge tube 111. No additional discharge tubing is used, thus helping to minimize the connection length between bulb pump 109 and discharge orifice 113. The discharge check valve 112 can be a duckbill-type check valve. This type of single piece check valve comprises: a body 404 that fits directly over the barb of discharge tube 111; a tapered discharge nozzle 405 that, when closed, acts as a check valve and, when opened, acts as a nozzle forming and directing the desired type of spray pattern; and a discharge orifice 113 to dispense the hand sanitizer into the palm. Locating all of these features within a one-piece check valve further minimize the connection length between pump 109 and discharge orifice 113.

Figure 5A:
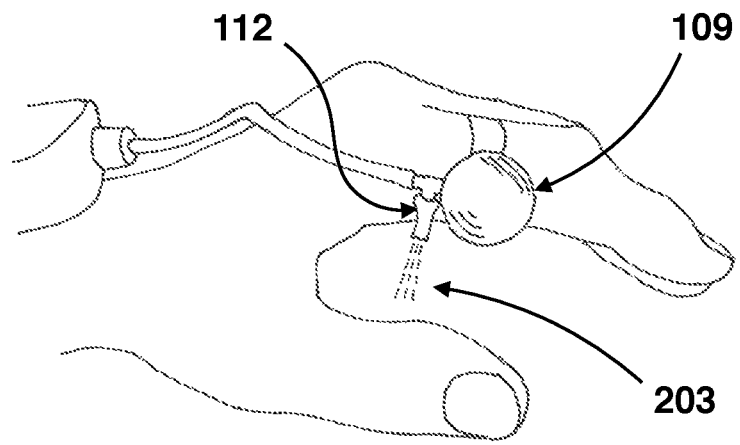
FIG. 5A is a perspective view of a dispensing bulb pump mounted on a left index finger.
Figure 5B:
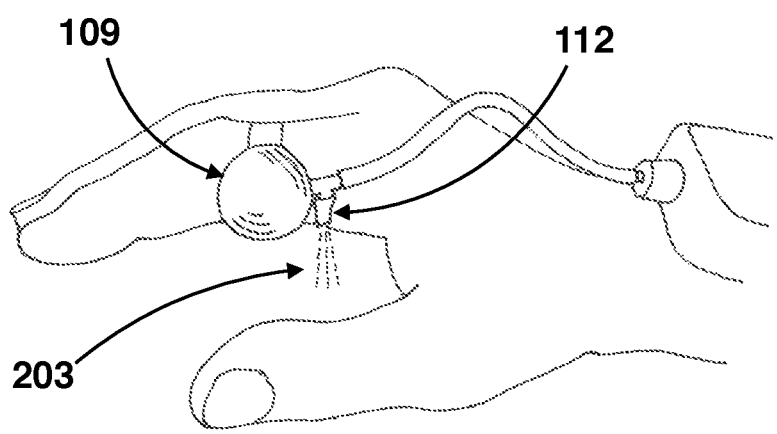
FIG. 5B is a perspective view of a dispensing bulb pump mounted on a right index finger.

FIG. 5A shows that when bulb pump 109 is mounted on a left index finger, the discharge check valve 112, which includes discharge nozzle 403 and discharge orifice 113, must be rotated to the right side 504 of bulb pump 109 in order to direct sanitizer spray stream 203 towards the palm. Conversely, as shown in FIG. 5B, when bulb pump 109 is mounted on a right index finger, discharge check valve 112 must be rotated to the left side 503 of bulb pump 109 in order to direct sanitizer spray stream 203 towards the palm. A discharge orifice that can be re-directed from side-to-side is thus necessary in order for the finger-mounted bulb pump, and in turn for the hand decontamination system, to be usable on both left and right extremities. In the embodiment shown in FIG. 4, this discharge orifice re-direction is made possible by the mounting of discharge check valve 112 on discharge tube 111. As the discharge tube 111 is a branch of the T-fitting 401, rotating T-fitting 401 about its insertion into tube port 305 of bulb pump 109 also rotates discharge tube 111, and in turn check valve 112.

A means for attaching or mounting a bulb pump to this index-finger, radial-side, proximal phalanx surface must be sufficiently stable to prevent undesired axial rotation and longitudinal slippage about the finger and to provide a firm surface against which the thumb can compress the bulb pump. Additionally, any pump mount must be able to accommodate a range of finger sizes.

FIG. 4 shows one embodiment meeting these parameters in the form of an adjustable-ring pump mount 110. As with decorative adjustable-ring jewelry, the adjustable-ring pump mount 110 also has an adjustable band 201 and a mounting surface 202, but in this case the mounting surface is for the attachment of bulb pump 109 rather than jewels. The adjustable ring mount 110 is typically constructed of a malleable metal with a flat or round cross-section. The adjustable ring mount 110 can be easily expanded in diameter to fit an individual's particular ring size, slips off and on easily, does not impede hand function, and is as comfortable as similarly-sized, adjustable-ring jewelry.

A hand decontamination system requires a fluid reservoir for containing hand sanitizer fluid. The fluid reservoir must be capable of supplying sanitizer fluid to the dispensing bulb pump regardless of the position of the components of the hand decontamination system relative to each other and to the vertical. For this reason, air must not be admitted into the fluid reservoir to replace withdrawn fluid; otherwise the pump could pump air rather than sanitizer fluid. Therefore, the reservoir must be able to collapse as fluid is withdrawn.

Figure 6:
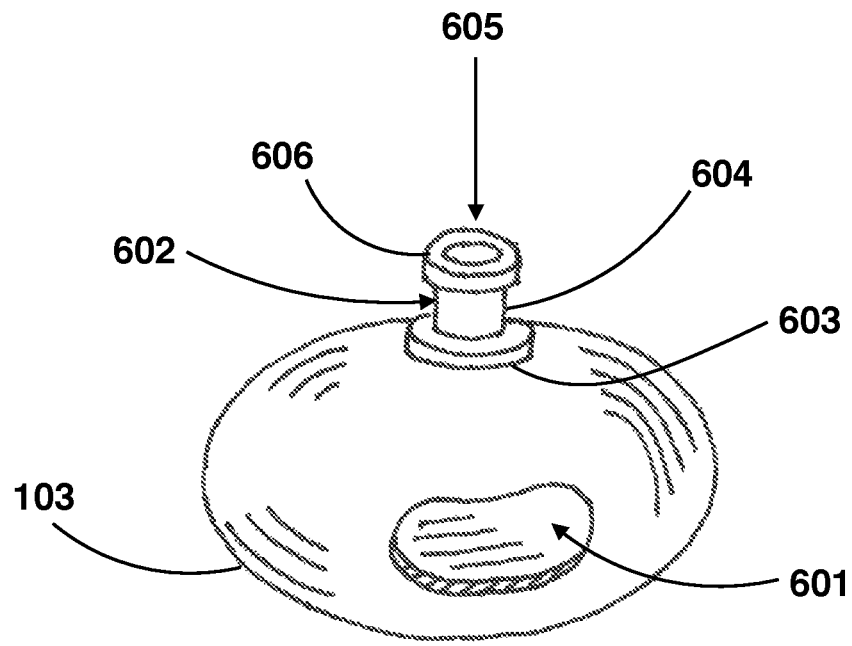
FIG. 6 is a perspective view of a collapsible fluid reservoir bag.

FIG. 6 shows one embodiment of a collapsible fluid reservoir in the form of a flexible plastic bag, e.g. the fluid reservoir bag 103, having an interior cavity 601. Access to the interior cavity for filling or withdrawing fluid from the reservoir bag 103 is provided by one or more bag ports 602. A bag port is typically formed as a single piece of plastic with a sealing flange 603 to which a fluid reservoir bag 103 can be thermally sealed in a water-tight fashion. A tubular port neck 604 forms a cylindrical port hole 605 and is contiguous with the interior cavity 601 of fluid reservoir bag 103. A bag port may incorporate a neck flange 606 to facilitate retaining a cap or plug used for sealing port hole 605 after fluid reservoir bag 103 is filled with sanitizer fluid.

Figure 7A:
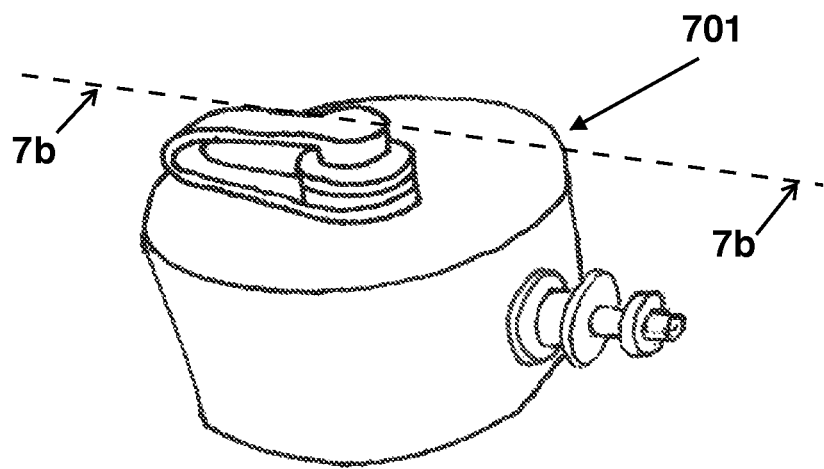
FIG. 7A is a perspective view of a fluid reservoir assembly having a filler bag port and a supply bag port.
Figure 7B:
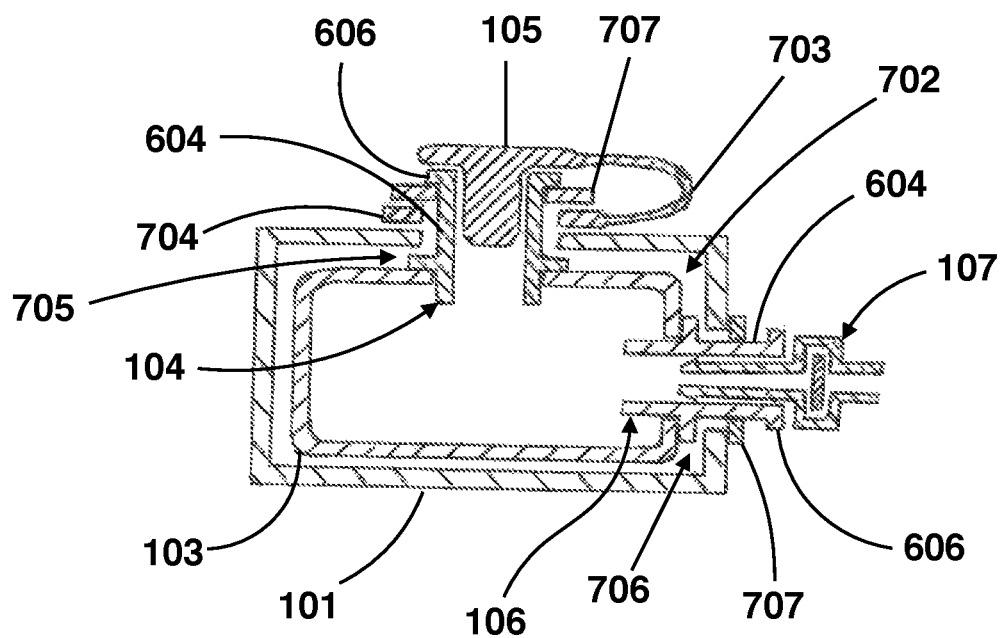
FIG. 7B is a sectional view of a fluid reservoir assembly having a filler bag port and a supply bag port.

In order to protect the collapsible fluid reservoir bag 103 from undesired squeezing or pressure, the bag 103 may be contained within a rigid reservoir housing, thus forming a fluid reservoir assembly. FIGS. 7A and 7B show a first embodiment of a fluid reservoir assembly 701 having a rigid reservoir housing 101 enclosing an interior cavity 702. Located within interior cavity 702 of reservoir housing 101, the collapsible fluid reservoir bag 103 has a filler bag port 104 that fills the fluid reservoir bag 103 with sanitizer fluid. Meanwhile, a supply bag port 106 supplies sanitizer fluid to the dispensing pump. The filler bag port 104 is sealable by the filler port plug 105. The filler port plug 105 may incorporate a tether 703 having at its end a tether ring 704 that fits over filler neck 604 and is retained by neck flange 606, thus preventing accidental plug loss. Filler ports may be sealed with alternative devices including, but not limited to, push-on, screw-on, or snap-on caps or plugs. Intake check valve 107 inserts into supply bag port 106 thus connecting fluid reservoir 103 to supply tubing 108 FIG. 1 and, in turn, to the dispensing bulb pump 109 FIG. 1.

The reservoir housing may be constructed of a rigid formable plastic such as ABS or any other similarly rigid material. The housing may be constructed in two sections, allowing the reservoir bag to be properly positioned in relation to the housing sections which are then assembled together. The housing sections may be assembled in a permanent fashion, or may be assembled in a reversible fashion when the ability to repair or replace the reservoir bag is desired. A reservoir housing may have one or more openings to provide access to a fluid reservoir bag contained therein. As shown in FIG. 7B, the port neck 604 of filler bag port 104 protrudes through a first filler bag port opening 705 in reservoir housing 101. The port neck 604 of supply bag port 106 protrudes through a second supply bag port opening 706 in reservoir housing 101. Port retainers 707 fit around port necks 604 of filler bag port 104 and supply bag port 106 and engage neck flanges 606 thus retaining the bag ports in position in the openings in reservoir housing 101. This feature prevents a bag port from falling back into the interior cavity of a reservoir housing rendering the bag port inaccessible. A reservoir housing may have additional openings to accommodate the passage or attachment of mounting straps or bands.

Figure 8A:
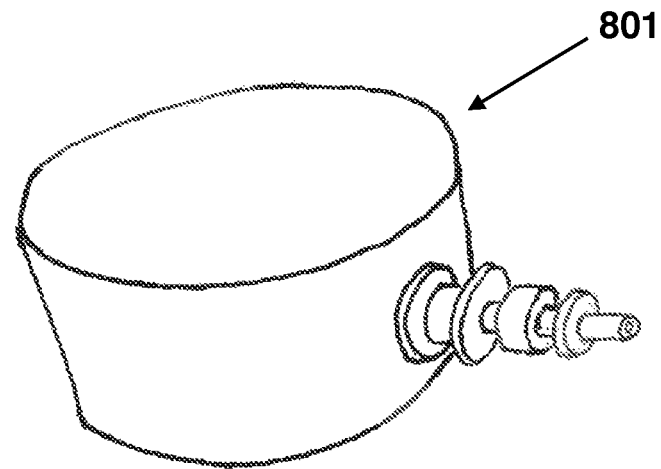
FIG. 8A is a perspective view of a fluid reservoir assembly having a multipurpose bag port.
Figure 8B:
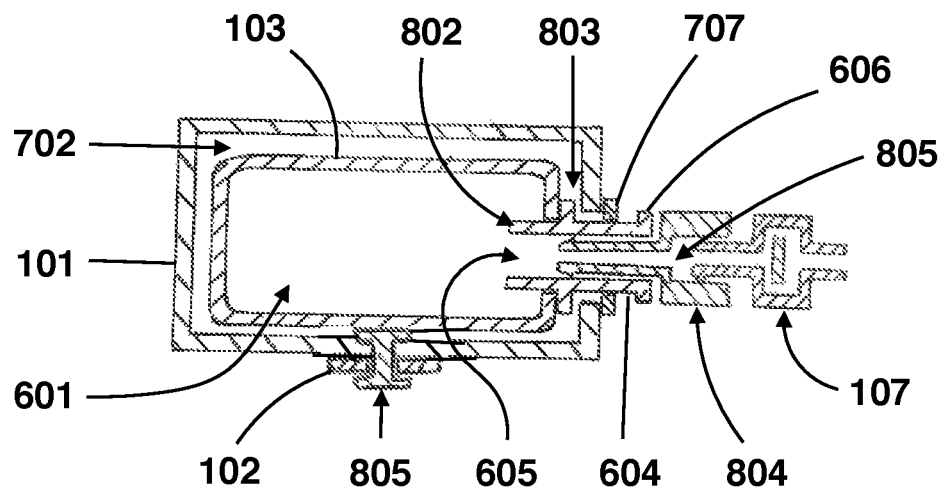
FIG. 8B is a sectional view of a fluid reservoir assembly having a multipurpose bag port.

FIGS. 8A and 8B show a second embodiment of a fluid reservoir assembly 801 having a rigid reservoir housing 101 enclosing an interior cavity 702. Located within interior cavity 702 of reservoir housing 101 is a collapsible fluid reservoir bag 103 having a single multipurpose bag port 802 having a port hole 605 contiguous with the interior cavity 601 of fluid reservoir bag 103. The port neck 604 of multipurpose bag port 802 protrudes through a single, multipurpose bag port opening 803 of reservoir housing 101. Port retainer 707 fits around port neck 604 and engages neck flange 606, thus retaining the bag port in position in the opening in reservoir housing 101. Multipurpose bag port 802 is sealable by a multipurpose bag port plug 804 having a central cannulation 805 that is contiguous with port hole 605 of multipurpose bag port 802 and, in turn, with the interior cavity 601 of fluid reservoir bag 103. Intake check valve 107 inserts into cannulation 805, thus connecting supply tubing 108 FIG. 1 to the interior cavity 601 of fluid reservoir bag 103. Multipurpose bag port plug 804 can be removed, permitting port hole 605 of multipurpose bag port 802 to be used to fill fluid reservoir bag 103 with sanitizer fluid. Multipurpose bag port 802 can thus serve both as a filler bag port and as a supply bag port.

Figure 9:
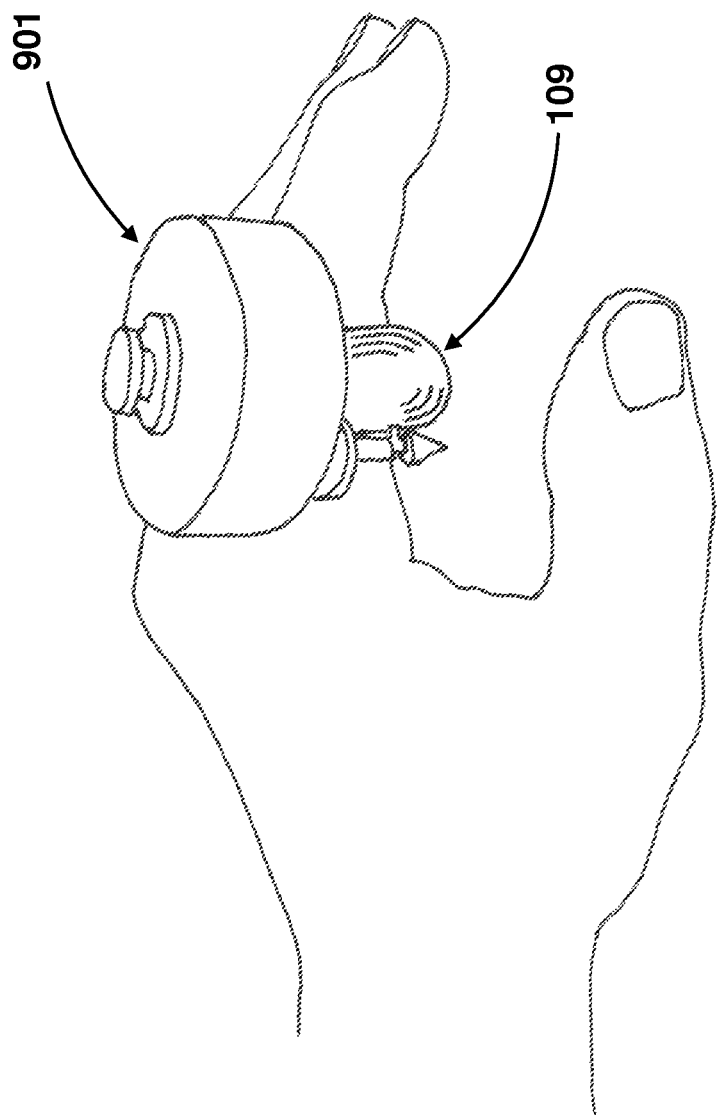
FIG. 9 is a perspective view of a finger-mounted fluid reservoir assembly.

Fluid reservoir location is dictated by the desired volume of hand sanitizer to be contained in the reservoir and the space available at a given anatomic location. FIG. 9 shows a first fluid reservoir embodiment wherein a small capacity fluid reservoir assembly 901 is located on the dorsal surface of an index finger immediately adjacent to dispensing bulb pump 109 and shares the same mount 110 FIG. 1 as bulb pump 109. Being located on the dorsal surface of the finger, reservoir assembly 1001 will not impair touch, grip, or pinch hand functions and does not obstruct access of the thumb to bulb pump 109. This dorsal finger location also keeps reservoir assembly 1001 away from the touch, grip, and pinch surfaces that are at greatest risk of contamination. This finger-mounted fluid reservoir assembly 901 must not be so large as to overhang the index finger to a degree that impinges on the thumb. The relatively small capacity of fluid reservoir assembly 901 is offset by the ease of putting on and taking off the pump and reservoir assemblies as a single unit.

Figure 10A:
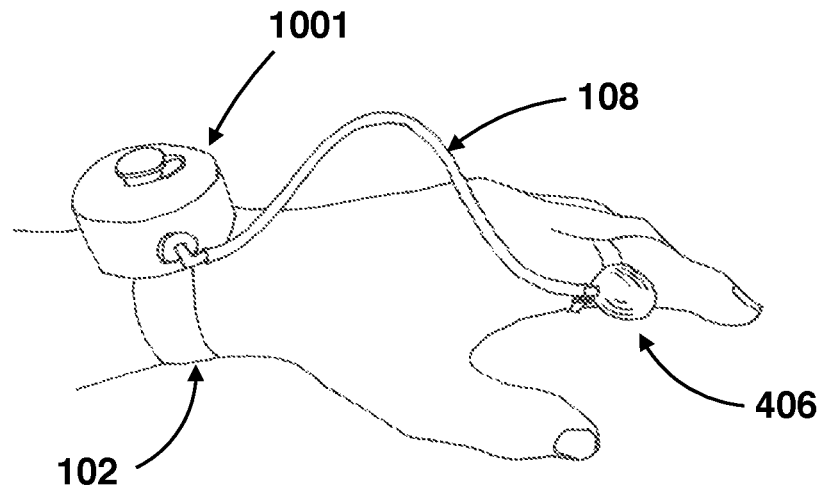
FIG. 10A is a perspective view of a wrist-mounted fluid reservoir assembly in an un-rotated position.
Figure 10B:
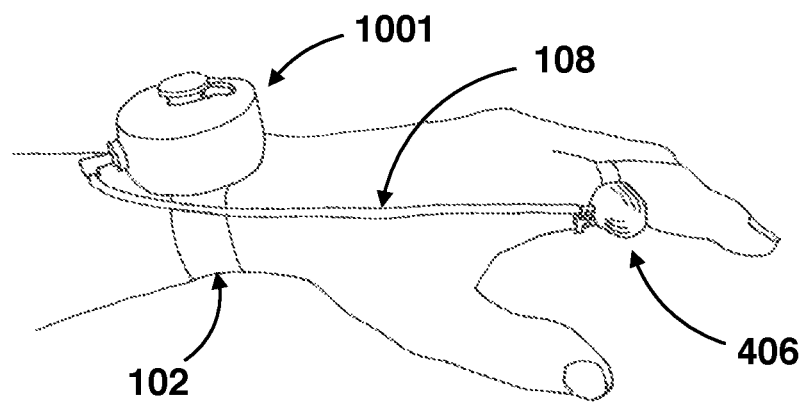
FIG. 10B is a perspective view of a wrist-mounted fluid reservoir assembly in a rotated position.

FIG. 10A shows a second fluid reservoir embodiment wherein a medium capacity fluid reservoir assembly 1001 is located on the dorsal surface of a wrist where more space is available for a larger capacity fluid reservoir than on the dorsal surface of an index finger. This wrist fluid reservoir location is removed from the index finger pump assembly location. Therefore, a longer supply tubing 108 running across the back of the hand is required. One advantage of a remote-mounted fluid reservoir, such as wrist-mounted fluid reservoir assembly 1001, is that it is located away from the hand and therefore at less risk of being cross-contaminated. Mounting strap 102, similar to ones used with a wristwatch, can provide a familiar means of attaching fluid reservoir assembly 1001 to the wrist. Fluid reservoir assembly 1001 is attached, followed by bulb pump assembly 406. Excess slack can be left in supply tube 108. As shown in FIG. 8B, a reservoir housing 101 can be attached to the mounting strap 102 by a rivet 805. As shown in FIG. 10B, this single rivet attachment of fluid reservoir assembly 1001 to the mounting strap 102 can allow reservoir assembly 1001 to be rotated relative to mounting strap 102 about rivet 805, thus taking up the excess slack in supply tube 108.

Figure 11:
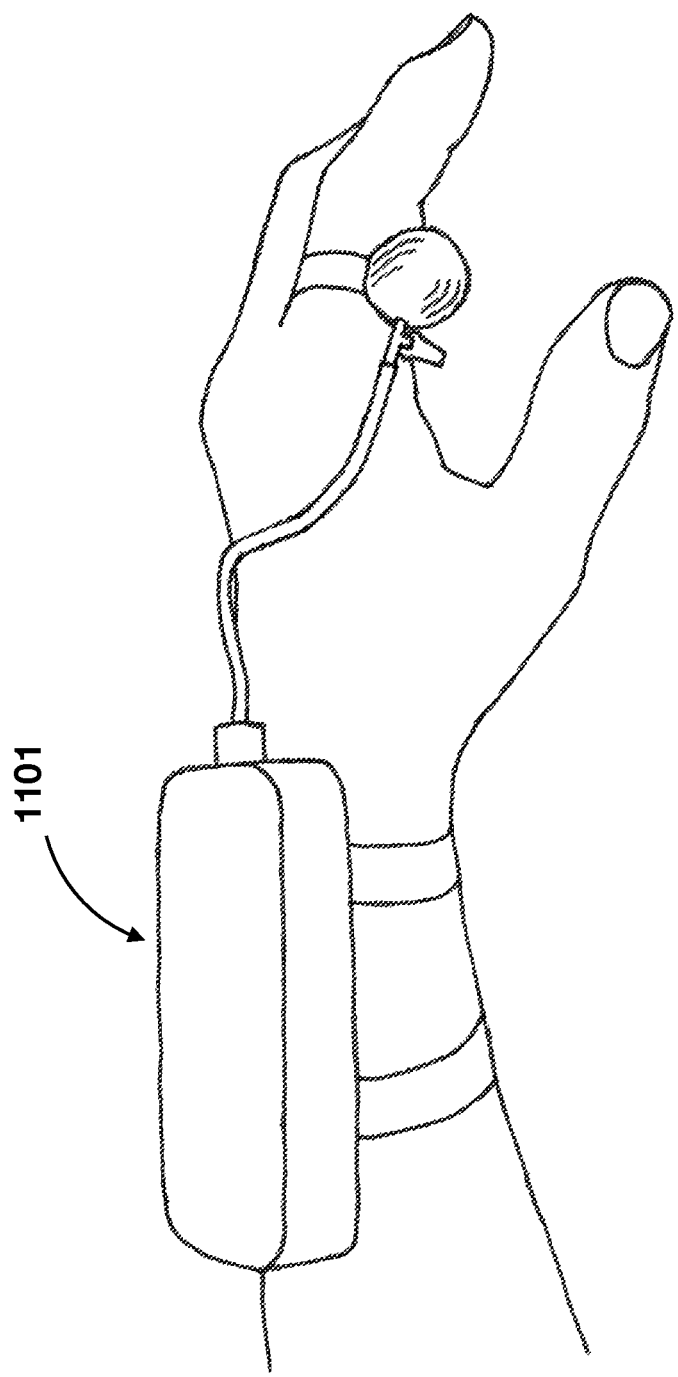
FIG. 11 is a perspective view of a forearm-mounted fluid reservoir assembly.

FIG. 11 shows a third fluid reservoir embodiment wherein a large capacity fluid reservoir assembly 1101 is located on the dorsal surface of a forearm where more space is available for a larger capacity fluid reservoir than on the dorsal surface of a wrist. Being remote-mounted, forearm-mounted fluid reservoir assembly 1101 is at less risk of cross-contamination. Being of larger capacity, forearm-mounted fluid reservoir assembly 1101 can be useful in situations requiring frequent hand decontamination, such as health care settings, or long periods of time without access to refills, such as long periods of travel.

It is anticipated that various changes may be made in the arrangement and operation of the system of the present embodiments herein without departing from the spirit and scope of the embodiments herein, as defined by the following claims. While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A wearable hand decontamination system for dispensing hand sanitizer fluid, comprising:
    a finger-mounted, manually-operable pump configured to be operable by a finger on the same hand as the finger to which the pump is mounted;
    the pump being configured for dispensing hand sanitizer fluid into the same hand as that on which the pump is located;
    a collapsible fluid reservoir bag having an interior cavity located adjacent to the fluid reservoir bag suitable for containing hand sanitizer fluid, the fluid reservoir bag being water-tight and air sealed and thus does not admit air;
    a supply tubing connecting the fluid reservoir bag to the pump;
    a one-way check valve located within the supply tubing for controlling the direction of fluid flow between the fluid reservoir bag and the pump;
    a discharge tubing connecting the pump to a discharge orifice; and
    a one-way discharge check valve for controlling the direction of fluid flow between the pump and the discharge orifice;
    wherein a contaminated hand can dispense hand sanitizer directly into the palm of that contaminated hand.

2. The system of claim 1, further comprising:
    the pump is a bulb pump.

3. The system of claim 1, further comprising:
    the pump is a piston pump.

4. The system of claim 1, further comprising:
    the fluid reservoir bag having a filler bag port for filling the fluid reservoir bag with hand sanitizer fluid; and
    the fluid reservoir bag having a supply bag port for supplying hand sanitizer fluid to the pump.

5. The system of claim 1, further comprising:
    the fluid reservoir bag having a multipurpose bag port for filling the fluid reservoir bag with hand sanitizer fluid and for supplying hand sanitizer fluid to the pump.

6. The system of claim 2, further comprising:
    the fluid reservoir bag being contained within the interior cavity of a reservoir housing constructed of a rigid material preventing external compression of the fluid reservoir bag; and
    the fluid reservoir bag and reservoir housing comprising a fluid reservoir assembly.

7. The system of claim 6, further comprising:
    the reservoir housing having a first filler bag port opening for accessing the filler bag port.

8. The system of claim 6, further comprising:
    the reservoir housing having a single multipurpose bag port opening for accessing the multipurpose bag port.

9. The system of claim 7, further comprising:
    the filler bag port having a port neck protruding through the filler bag port opening in the reservoir housing;

the port neck having a neck flange for engaging a port retainer for maintaining the filler bag port in position in the filler bag port opening in the reservoir housing;

the supply bag port having a port neck protruding through the supply bag port opening in the reservoir housing; and the port neck having a neck flange for engaging a port retainer for maintaining the supply bag port in position in the supply bag port opening in the reservoir housing.

10. The system of claim 8, further comprising:

the multipurpose bag port having a port neck protruding through the multipurpose bag port opening in the reservoir housing; and the port neck having a neck flange for engaging a port retainer for maintaining the multipurpose bag port in position in the multipurpose bag port opening in the reservoir housing.

11. The system of claim 4, further comprising:

the filler bag port having a port hole contiguous with the interior cavity of the fluid reservoir bag;

the port hole being reversibly sealable with a plug;

the plug being configurable for push-on, screw-on, or snap-on attachment; and the plug or cap being attachable to the filler bag port by a tether.

12. The system of claim 1, further comprising:

the finger-mounted pump being attachable to the finger via an adjustable ring mechanism whereby the diameter of the ring mechanism can be adjusted to fit different ring sizes of the wearers.

13. The system of claim 1, further comprising:

the one-way discharge check valve is a duckbill check valve.

14. The system of claim 1, further comprising:

the discharge orifice being re-directable side-to-side in relation to the pump allowing the identical hand decontamination system to be used on either left or right hand.

15. The system of claim 6, further comprising:

the hand decontamination system being mounted adjacent to the finger-mounted pump, utilizing the same mounting surface as the finger-mounted pump.

16. The system of claim 6, further comprising:

the hand decontamination system being mounted on the wrist and remote from the finger-mounted pump; and the hand decontamination system being mounted on the wrist using a mounting strap.

17. The system of claim 16, further comprising:

the hand decontamination system being rotatable relative to the mounting strap allowing excess slack in the supply tubing to be taken up.

18. The system of claim 6, further comprising:

the hand decontamination system being mounted on the forearm and remote from the finger-mounted pump.

19. The system of claim 7, further comprising:

the hand decontamination system having a second supply bag port opening for accessing the supply bag port.

* * * * *